US005773989A

United States Patent [19]
Edelman et al.

[11] Patent Number: 5,773,989
[45] Date of Patent: Jun. 30, 1998

[54] MEASUREMENT OF THE MOBILE ION CONCENTRATION IN THE OXIDE LAYER OF A SEMICONDUCTOR WAFER

[75] Inventors: Piotr Edelman; Andrew M. Hoff; Lubek Jastrzebski; Jacek Lagowski, all of Tampa, Fla.

[73] Assignees: University of South Florida; Semiconductor Diagnostics, Inc., both of Tampa, Fla.

[21] Appl. No.: 502,660

[22] Filed: Jul. 14, 1995

[51] Int. Cl.$^6$ ................................................ G01R 31/00
[52] U.S. Cl. .......................... 324/765; 324/769; 437/8; 29/838
[58] Field of Search ................................. 324/767, 765, 324/71.3, 769; 437/8; 29/838, 844

[56] References Cited

U.S. PATENT DOCUMENTS

| | | | |
|---|---|---|---|
| 4,168,432 | 9/1979 | Williams et al. | 250/370 |
| 4,599,558 | 7/1986 | Castellano, Jr. et al. | 324/158 R |
| 4,744,833 | 5/1988 | Cooper et al. | 134/1 |
| 4,812,756 | 3/1989 | Curtis et al. | 324/158 R |
| 4,950,977 | 8/1990 | Garcia et al. | 324/71.1 |
| 4,978,915 | 12/1990 | Andrews, Jr. et al. | 324/73.1 |
| 5,216,362 | 6/1993 | Verkuil | 324/158 D |
| 5,394,101 | 2/1995 | Mitros | 324/769 |
| 5,410,162 | 4/1995 | Tigelaar | 324/765 |
| 5,498,974 | 3/1996 | Verkuil | 324/767 |

OTHER PUBLICATIONS

Verkuil, "Contactless Alternatives to MOS Charge Measurements", Abstract No. 525, Fall Meeting 1980, pp.1313–1315.

R.L. Verkuil et al., *Extended Abstracts*, vol. 88–1, "A Contactless Alternative to MOS Charge Measurements By Means Of A Corona–Oxide–Semiconductor (COS) Technique", Abstract No. 169, Spring Meeting, Atlanta, Georgia, May 15–20, 1988, pp. 261–262.

D. Schroeder, *Semiconductor Material and Device Characterization*, "Oxide and Interface Trapped Charge", Chapter 6, 1990, pp. 224–247, 262–267, 290–291.

P. Edelman et al., *Optical Characterization Techniques for High–Performance Microelectronic Device Manufacturing*, "New approach to measuring oxide charge and mobile ion concentration", vol. 2337, pp. 154–164, Austin, Texas, Oct. 20, 1994.

Bickley, "Quantox™ Non–Contact Oxide Monitoring System" *A Keithley Technology Paper*, 1995.

Horner et al., "Monitoring electrically active contaminants to asses oxide quality" *Solid State Technology*, Jun., 1995.

Horner et al., "COS–Based Q–V Testing: In–Lin Options for Oxide Charge Monitoring" *IEEE/SEMI Advanced Semiconductor Manufacturing Conference*, 1995.

Jastrzebski and Edelman, "Real–Time, preparation–free imaging of mobile charge in $SiO_2$" Presented at *Optical Characterization Techniques for High–Performance Microelectronic Manufacturing*, Oct. 16–17, 1996.

Keithley Instruments, "Quantox™ Engineering Manual" Feb. 1996.

*Primary Examiner*—Ernest F. Karlsen
*Assistant Examiner*—Barry C. Bowser
*Attorney, Agent, or Firm*—Fish & Richardson P.C.

[57] ABSTRACT

A method and apparatus for measuring the concentration of mobile ions in the oxide layer of a semiconductor wafer from the contact potential shift caused by ion drift across the oxide that includes depositing charge (e.g., using a corona discharge device) on the surface of the oxide and heating the wafer to allow mobile ions in the oxide (especially $Na^+$) to drift. The difference in the contact potential measured before and after heating provides an indication of the mobile ion concentration in the oxide layer.

24 Claims, 9 Drawing Sheets

INITIAL STATE
TEMP. 22°C

POSITIVE CORONA
CHARGING
TEMP. 22°C

CORONA
TEMPERATURE
STRESS
TEMP 200°C, 4 MIN.
AND COOLING TO
TEMP. 22°C

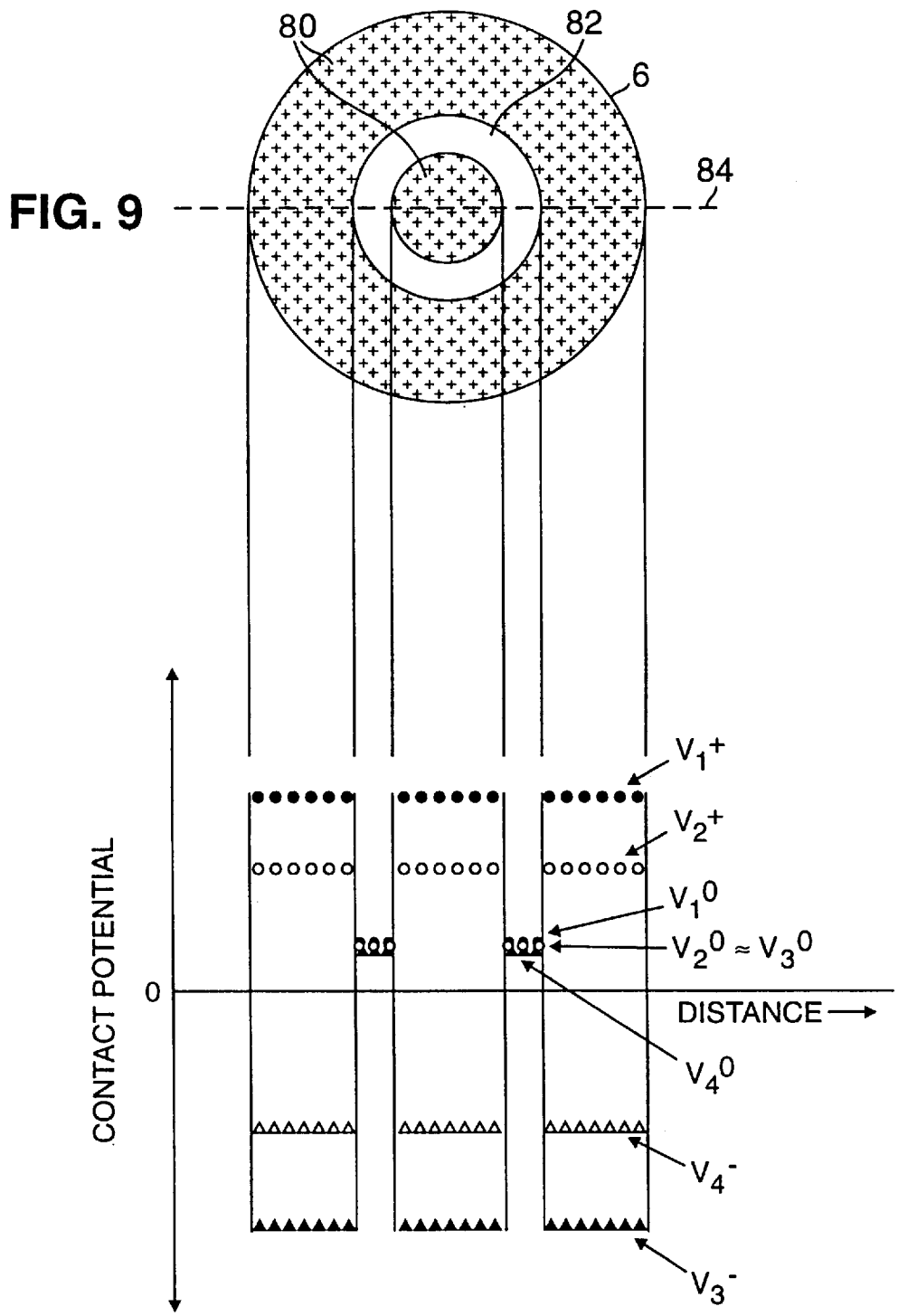

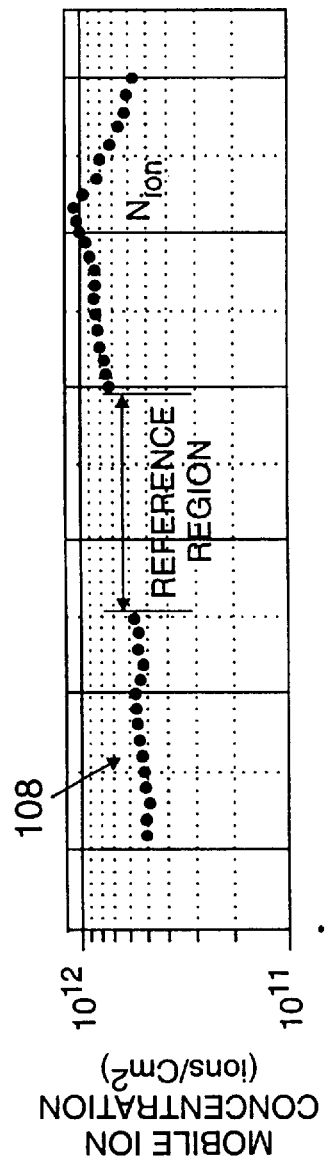
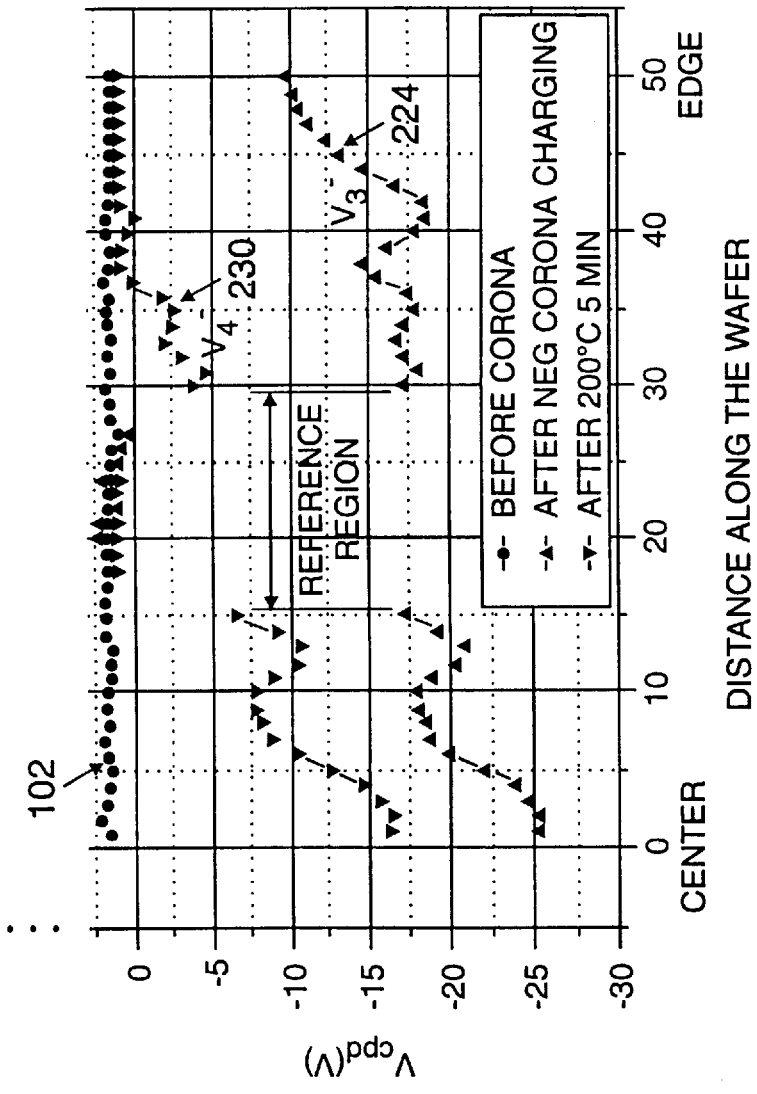
FIG. 11A
FIG. 11B

MEASUREMENT OF THE MOBILE ION CONCENTRATION IN THE OXIDE LAYER OF A SEMICONDUCTOR WAFER

BACKGROUND OF THE INVENTION

The invention relates to semiconductor wafer testing.

Mobile ion contaminants within an oxide layer can cause problems in the manufacture and performance of integrated circuits. For example, ionic impurities such as $Na^+$, $Li^+$, $K^+$ are often introduced within a $SiO_2$ oxide layer disposed over a silicon semiconductor wafer during high temperature processing. The most common technique for measuring the concentration of mobile ions in the oxide layer include the capacitance-voltage (CV) method and the triangular voltage sweep (TVS) method. These methods are described in D. K. Schroder, *Semiconductor Material and Device Characterization*, John Wiley & Sons, Inc. (1990), pp. 263–267, hereby incorporated by reference.

Generally, these methods include preparation of metal oxide semiconductors (MOS) capacitor patterns on test wafers and applying a voltage to a metal while heating the wafer to move the ions. In the CV methods, the mobile ion concentration is determined from the differences in capacitance-voltage characteristics caused by a drift of ions; and specifically by the shift in so-called "flat band voltage". In the TVS method, mobile ion concentration is determined from the electric current component due to mobile ion drift across the oxide.

In another technique, a combination of surface photovoltage measurements and corona charging steps was used in order to determine "flat band voltage" shift without preparation of MOS capacitors. Mobile charge drift, in this method, was induced by corona charging of the oxide surface and by heating the wafer. This technique is described in R. L. Verkuil, *Contactless Alternatives to MOS Charge Measurement*, Extended abstracts 80-1 No. 525, Fall Meeting of the Electrochemical Society, October 1980, pp. 1313–1315, (1980), and R. L. Verkuil and M. S. Fung, *A Contactless Alternative to MOS Charge Measurements by Means of a Corona-Oxide-Semiconductor (COS) Technique*. Extended Abstracts 88-1 No. 169, Spring Meeting of the Electrochemical Society, May 1988, pp. 261–262, (1988).

SUMMARY OF THE INVENTION

This invention relates to determining mobile ion concentration directly from a change in the contact potential value caused by the mobile ion redistribution toward or away from the top of the oxide surface.

In one aspect, the invention features determining the mobile ion concentration within an oxide layer deposited on a surface of semiconductor wafer in the following manner. A charge is deposited on a portion of the surface of the oxide layer to change the electric field in the oxide layer. This is done at a low (e.g. room) temperature, at which ion impurities do not move within the oxide layer. The contact potential on the surface of the oxide layer after deposition of the charge is then measured. The semiconductor wafer with oxide layer is heated to a pre-determined temperature sufficient to activate drift (i.e., motion of charge caused by an electric field) of (positive) ion impurities toward or away from the top of the oxide surface for negative or positive corona charge. The contact potential shift before and after annealing is determined. The mobile ion concentration within the oxide layer is then determined from this shift.

In preferred embodiments, the corona charging is done in such a way that a region on the wafer surface is left with no deposited charge. This region serves as a reference. The measurements of contact potential changes in this region, after wafer heating, are used to correct results caused by factors other than the mobile ion drift, such as desorption of wafer or decomposition of organic residue present on the wafer surface. Importantly, the measurements in the reference region also can serve to determine the contribution of accidental electrostatic charging of the wafer back surface and/or of the wafer chuck caused by wafer transport as the wafer is removed from and placed on the chuck. The accidental wafer charging may be enhanced in cases where the electrical contact wafer ground is only capacitive and the highly insulating $Sio_2$ layer is present on the wafer back surface.

In preferred embodiments, a semiconductor surface potential barrier is measured after corona charging both before and after annealing. The surface potential barrier does not change due to ion movement within the oxide. It does, however, change when the mobile ions are neutralized by electrons injected from the semiconductor. Interference from charge injection and ion neutralization is determined on the basis of both the contact potential and the semiconductor surface potential barrier of the wafer, permitting accurate determination of the mobile ion concentration.

In preferred embodiments, to further improve the precision of the measurement, a combination of positive corona charging and heating the wafer (to be referred to as positive "corona temperature stress", CTS) is followed by a negative corona temperature stress (or vice versa) and the mobile concentration is determined from the difference in the contact potential values after positive CTS and after negative CTS. During CTS, the semiconductor wafer is heated to a temperature typically in a range between 165°–200° C. and held at that temperature for a period typically between four and ten minutes.

In another aspect of the invention, a system for the measurement of mobile contaminant ion concentration in an oxide layer on a semiconductor wafer, that can be used in conjunction with the method described above, includes a charge deposition device (e.g., a corona discharge device) configured to deposit charge on the oxide surface, a temperature stress device (e.g. a heater) adapted to receive and heat the wafer to a temperature sufficient to allow the drift of ions within the oxide layer. The temperature stress device may also include a cooler to reduce the wafer's temperature to a temperature below that at which the ions drift. This system also includes a measurement device configured to measure the change in contact potential on the oxide surface. The measurement device may be, for example, a vibrating Kelvin probe voltmeter or a Monroe-type electrostatic voltmeter.

In preferred embodiments, the invention further includes one or more of the following features. A device for measuring the surface potential barrier in the semiconductor underlying the oxide layer (e.g., a contactless SPV probe and laser-pulsed radiation). This is used to determine a contribution from mobile ion neutralization during corona temperature stress. A robotic handler is used to move the semiconductor wafer between the corona charging device, temperature stress device, heater, and measurement device. The measurement device contains a wafer moving stage enabling measurement at any pre-selected point on the wafer surface or scanning and mapping of the wafer. A computer is provided to control the robotic handler and to transmit control signals to and receive data signals from the corona charge deposition device, temperature stress device, and measurement device and to automatically calculate mobile ion concentration.

Embodiments may include one or more of the following advantages. The system provides a fast, accurate, and reliable technique for measuring the mobile ion concentration within the oxide layer of a semiconductor wafer. The technique is non-destructive and during the entire cycle the wafer is contacted only from the back side for the purpose of holding, moving, heating, and cooling the wafer. Thus, the wafer can be characterized without having to sacrifice a portion of the wafer. Moreover, because the technique can be performed relatively quickly, the mobile ion concentration can be mapped on the entire region (with the exception of the uncharged reference region) rather than in only particular points on the wafer. The technique makes possible the scanning or mapping of the mobile ion distribution over the entire wafer surface in a realistic time, e.g., about 10 to 20 minutes for an 8 inch diameter size wafer.

Further features, aspects, and advantages, follow.

BRIEF DESCRIPTION OF THE DRAWINGS

FIG. 9 is a top view of the semiconductor wafer showing regions of deposited charge.

FIG. 10 is a graph of contact potential as a function of distance across the wafer of FIG. 9.

Figs. 11A and 11B are plots of the contact potential difference and mobile ion concentration as a function of distance across a silicon wafer, respectively, for a semiconductor substrate with an oxide layer having ionic impurities.

DESCRIPTION OF THE PREFERRED EMBODIMENTS

Figure 1:
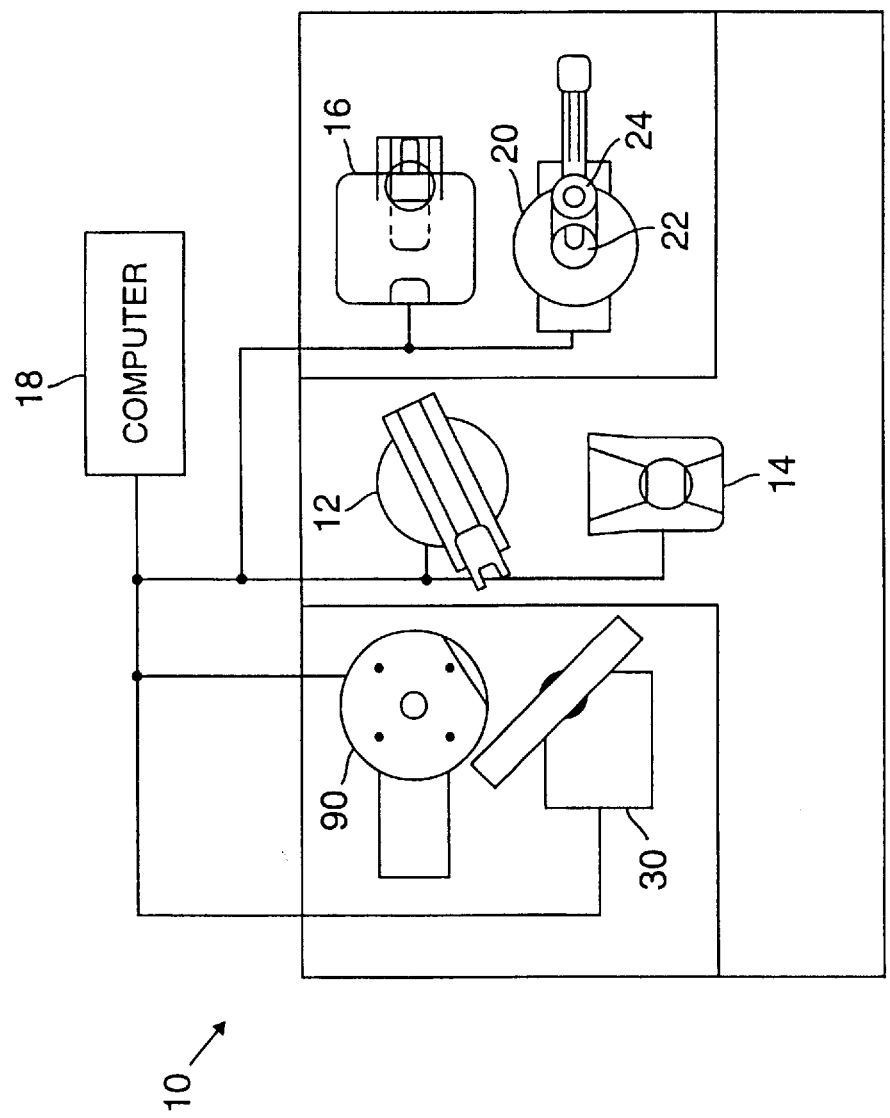
FIG. 1 is a plan view of the measurement system according to the invention.

Referring to FIG. 1, a computer controlled test system 10 for the measurement of mobile ion concentration in an oxide layer deposited over a semiconductor wafer is shown. Test system 10 includes a charge measurement station 20, a corona charging station 30, a temperature stress station 90, a prealigner station 16, and a robotic wafer handler 12 for moving the wafer about the stations of the system.

Figure 3:
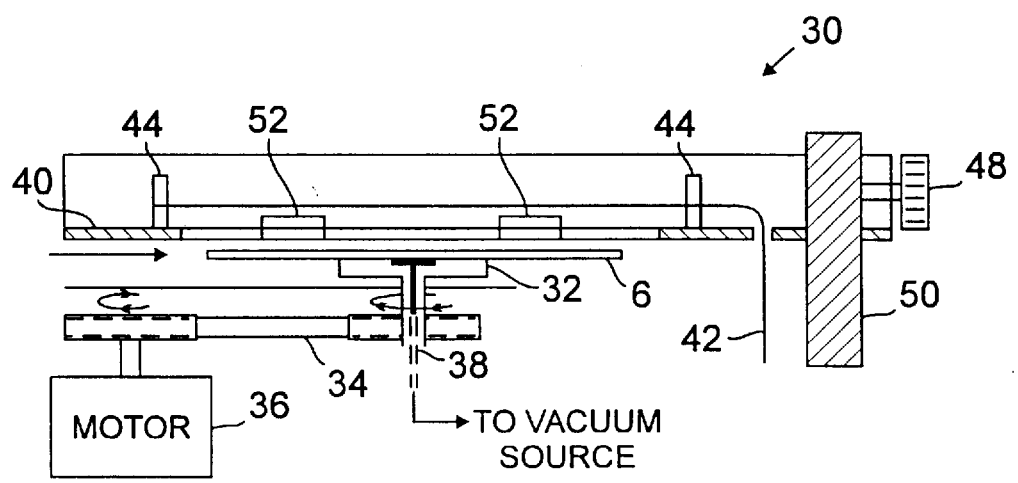
FIG. 3 is a side view of the corona discharge device of the measurement system of FIG. 1.

The charge measurement station 20 has a Kelvin probe sensor or a Monroe-type sensor 22 which is used to measure the contact potential of the oxide surface with respect to the reference electrode. In use, sensor 22 is separated from wafer 6 by an air gap a fraction of a millimeter wide (FIG. 3). These sensor types are described, respectively, in G. W. Reedyk and M. M. Perlman: Journal of the Electrochemical Society, Vol. 115, p. 49 (1968); and in R. E. Vosteen: Conference Records, 1974 IEEE-IAS 9th Annual Meeting, p. 799, the entire contents of which are incorporated herein by reference. An example of a commercially available device is the Isoprobe model 162 by Monroe Electronics, Lyndonville, N.Y. 14098.

Charge measurement station 20 also includes a photovoltage transducer probe 24 for measuring the semiconductor surface potential of the wafer. As will be described in greater detail below, the semiconductor surface potential barrier can be used to detect a charging process interfering with the mobile charge concentration determination. A suitable probe and measurement of surface photovoltage is described in Lagowski U.S. Pat. No. 5,177,351 and in Lagowski, "Determining Long Minority Carrier Diffusion Length", U.S. application Ser. No. 08/312119, filed Aug. 26, 1994, the entire contents of which are incorporated herein by reference. A suitable device and method are also described in: P. Edelman, J. Lagowski, L. Jastrzebski, "Surface Charge Imaging in Semiconductor Wafers by Surface Photovoltage (SPV)" MRS Symposium Proceedings, 261, pp. 223 (1992), the entire contents of which are incorporated by reference.

Figure 2:
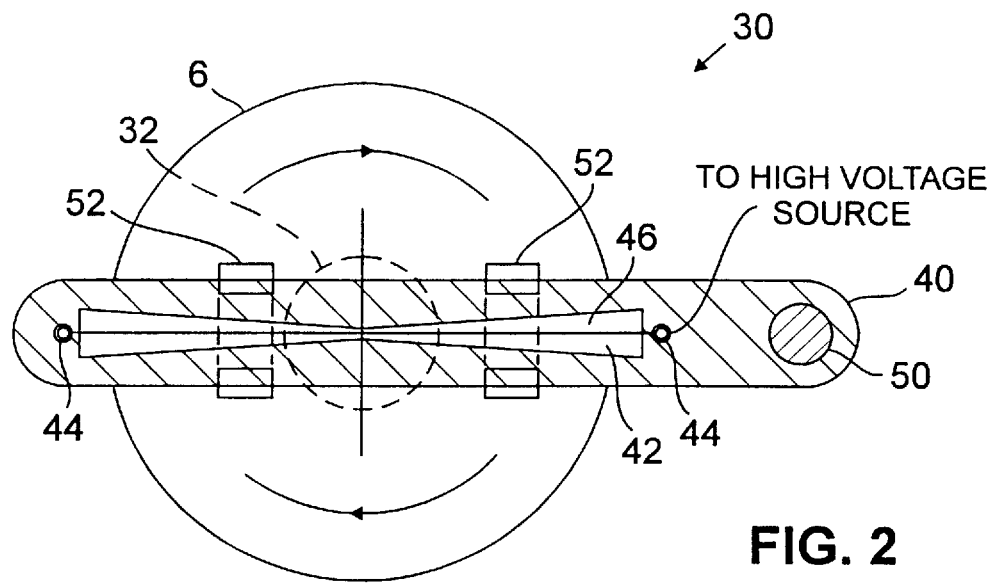
FIG. 2 is a top view of the corona discharge device of the measurement system of FIG. 1.

Referring as well to FIGS. 2 and 3, the corona discharge device 30 deposits charge on the oxide layer surface of the wafer. Corona charging station 30 includes a wafer chuck 32 which is rotated via a belt 34 connected to a motor 36. Silicon wafer 6 is held securely in place on wafer chuck 32 by vacuum provided from an external vacuum source (not shown) and through an aperture 38 passing through wafer chuck 32. An aluminum plate 40 is positioned between 2–3 mm above wafer 6 and serves as a ground terminal for a discharge wire 42 connected to a high voltage source (not shown). Wire 42 extends across the wafer between a pair of teflon posts 44 mounted on plate 40. Plate 40 includes a slotted aperture 46 wider at its ends and narrower at its center so that when the wafer is rotated, deposition of charge emitted from wire 42 through aperture 46 and onto wafer 6 is substantially uniform. The spacing of the wafer from plate 40 with respect to wafer 6 is adjusted by rotating knob 48 on mounting post 50. The dimensions of aperture 46 and spacing between plate 40 and wafer 6 are both determined empirically to provide the desired level and uniformity of charge on the wafer. For effective mobile ion drift at temperatures of about 165°–200° C., the electric field in the oxide should be typically $5 \times 10^5$ v/cm or higher. Such a field can be achieved by deposition of a charge of about $10^{12}$ ions/cm$^2$. In the corona charging device, the charge deposited is controlled by the charging time and the wafer rotation speed. The quantitative corona charging characteristics, e.g. the charge versus time and the charge versus rotation speed are determined empirically and are introduced into computer software, controlling the corona charging station.

Masking plates 52, fabricated of metal, are positioned across aperture 46 of plate 40 an equal distance from the center of the aperture to prevent deposition of charge over a ringed-shaped portion of the wafer. As will be discussed below, this ringed-shaped portion establishes a reference region 86 (FIG. 9) used in distinguishing between mobile ion drift and other effects of temperature stress on contact potential measurements.

System 10 also includes temperature stress station 90, for heating the wafer after depositing the charge, which contains two temperature-controlled wafer chucks. A heating chuck is provided by an electric heating plate for heating the wafer to a pre-selected temperature from e.g., 165°–200° C. A cooling chuck is provided by a water (or air) cooled aluminum plate which cools the wafer, e.g., to room temperature. Both heating and cooling chucks hold the wafer by means of a vacuum suction which assures good thermal contact. The chucks are placed one above the other (with a heating chuck on the top) and transport of the wafer from heating to cooling chuck is done by the robotic handler 12.

Test system 10 further includes a wafer cassette holder 14 for storing the semiconductor wafers to be tested and a prealigning stage 16 for accurate positioning of the wafer as it is moved from device to device, thereby minimizing positioning errors from measurement to measurement. The prealigner station 16 is used for pre-orientation of the wafer prior to measurement by using a notch or flat made by wafer manufacturers near the edge of the circular wafer for exactly that purpose. A computer 18 controls robotic wafer handler 12 and transmits controls signals to and receives data signals from cassette holder 14, charge measurement station 20, corona discharge device 30, and temperature stress station 90.

Measurement of Mobile Ions

Referring as well to FIGS. 4A–4C, 5A–5C, and 6A–6C, the system measures mobile ion concentrations in the oxide layer by measuring the contact potential V and the semiconductor surface potential barrier $V_s$, before and after ions are forced to redistribute in the oxide by drifting in the field created by corona change. Silicon wafer 6, having silicon dioxide layer 4, is shown in a cross-section in FIG. 4B and in FIGS. 5A–5C. Ionic impurities 70, primarily sodium (Na$^+$) but also potassium (K$^+$) and lithium (Li$^+$), are introduced into silicon dioxide layer 4 during elevated temperature processing. For the purpose of example, in FIG. 5A Na$^+$ions are illustrated as initially located near the top of the Sio$_2$ surface. These ionic impurities are immobile at room temperature. In system 10 the charge 72 (in this case, a positive charge), is deposited on the SiO$_2$ surface using the corona discharge device 30. Schematic representation of corresponding changes in silicon Sio$_2$ and of the energy band diagrams are shown in FIGS. 5A–5C and FIGS. 6A–6C.

Figure 6A:
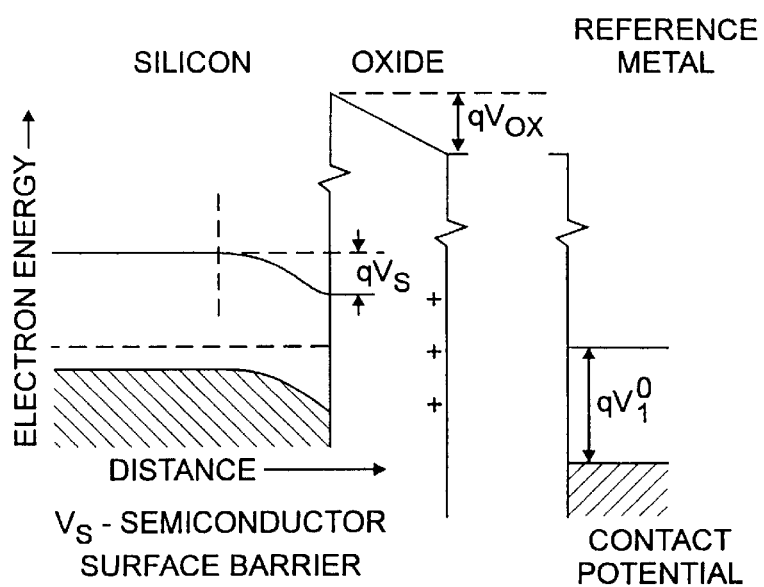
FIGS. 6A–6C are energy band diagrams corresponding to FIGS. 5A–5C respectively.
Figure 6B:
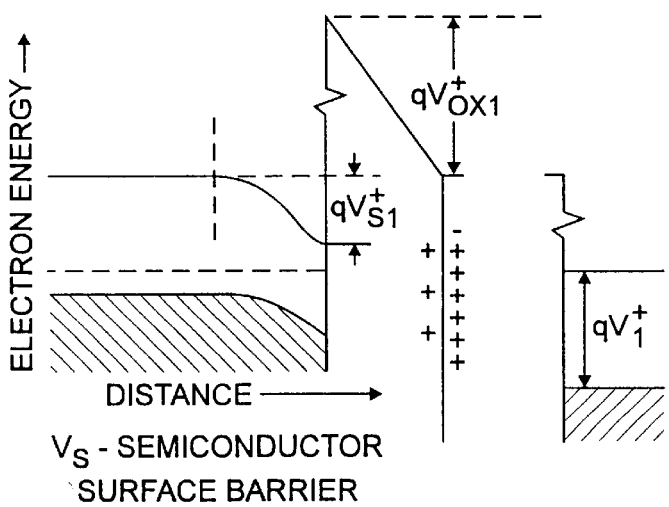
Figure 6C:
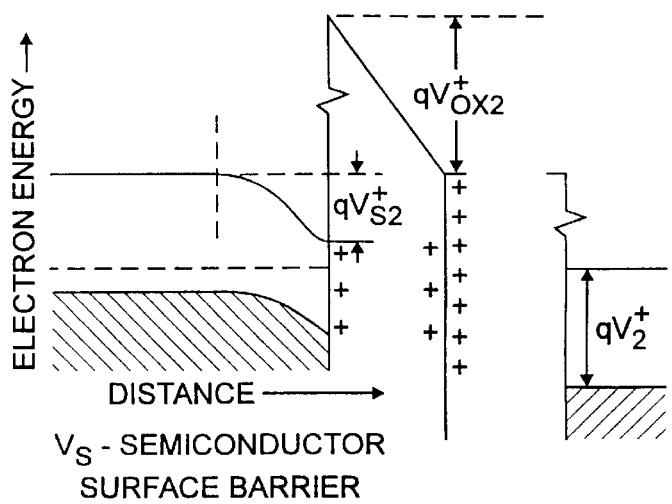

Referring particularly to FIGS. 6A–6C, the charge 72 changes two quantities: the value of the semiconductor surface barrier $V_s$ and the value of the potential drop across the oxide $V_{ox}^+$. The change of $V_s$ is typically only a fraction of a volt. The change of $V_{ox}$ may be a fraction of a volt for a thin, e.g., 100 Å A thick oxide, or by many volts for thicker oxides. The term $\Delta V_{ox} \approx \sigma_c \cdot d_{ox}/K_{ox}\epsilon_o$, where $\sigma_c$ is the corona charge per cm$^2$, $d_{ox}$ is the oxide thickness, $K_{ox}$ is the dielectric constant of Sio$_2$ and $\sigma_o$ is the permittivity of free space.

As illustrated in FIGS. 6A and 6B, the contact potential $V_i^+$change includes contribution from a change in $V_s$ and in $V_{ox}$. Silicon wafer 6 is then heated at temperature stress station 90 to a temperature sufficient to allow the ion impurities 70 to become mobile and move away from the top surface due to electrostatic repulsion by corona charge 72. This corona temperature stress causes a drift of the ionic impurities 70 to the silicon/silicon oxide interface 8 (FIG. 5C). As a result, a potential drop across the oxide decreases to a new value, $V_{ox2}^+$, which is lower than the pre-stress value, $V_{ox1}^+$. In the case of ideal mobile ion drift, the surface potential barrier does not change because its value is determined by the total surface charge (in this case, ionic charge plus corona charge) irrespective of the charge location with the oxide. If $V_{S2}^+ = V_{S1}^+$, then $V_{ox1}^+ - V_{ox2}^+ = V_1^+ - V_2^+$ and the mobile ion concentration can be determined from a difference $V_1^+ V_2^+$ in the contact potential value measured with the device 22.

If $V_{S2}^+ \neq V_{S1}^+$ and especially if a change is significant, then the contact potential change must be corrected for a change in the surface barrier. This may be caused by charge injection from a semiconductor into the oxide during corona temperature stress. Surface barrier corrections will be especially significant for thin oxides, e.g., of the thickness of 100Å and below, which are used as gate oxides in the most advanced silicon integrated circuits.

Figure 5A:
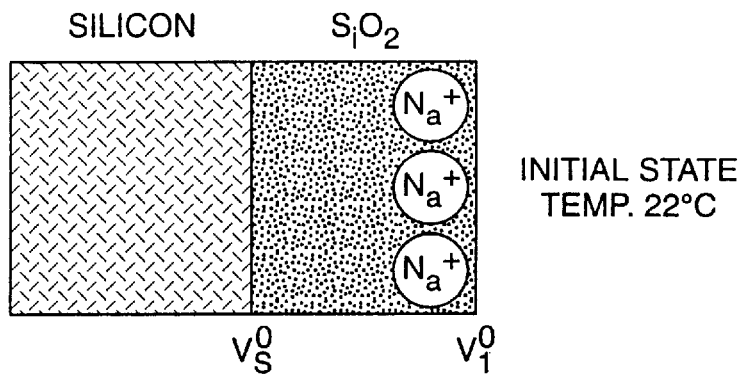
FIGS. 5A–5C are schematic representations of cross-sections of a semiconductor wafer having an oxide layer that illustrate the influence of an electric field on the distribution of mobile ions in the oxide layer.

The simple case of FIG. 5A, where mobile ions are initially located near the top of the Sio$_2$ surface, may not be representative of high temperature processed wafers. Therefore, a more accurate procedure for measuring mobile ion concentration incorporates sequential negative corona temperature stress and positive corona temperature stress. The negative corona temperature stress moves positive mobile ions 70 toward the top of the SiO$_2$ surface. The subsequent positive corona temperature stress is applied for determining the mobile ions concentration (in accord with FIGS. 5A–5C).

Information on initial distribution of mobile ions can be obtained by comparing the absolute magnitude of contact potential changes after the first negative corona temperature stress with those of the second positive corona temperature stress. Alternatively, a positive corona temperature stress can be used as the first step in the sequence creating ion distribution as shown in FIG. 5C. Then the negative corona temperature stress moves ions to the top of the surface as a second step. This positive-negative corona sequence is represented in FIG. 8.

Figure 5B:
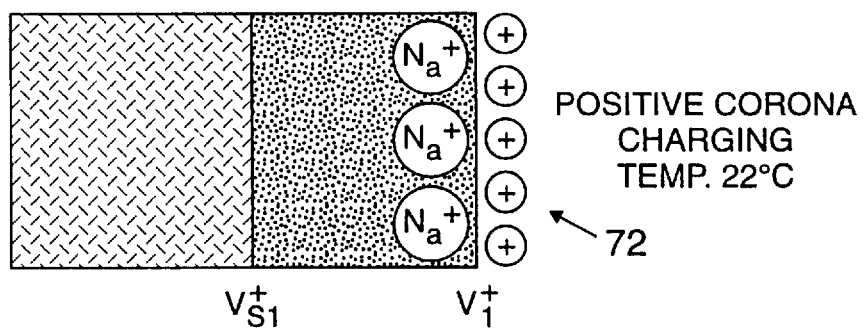
Figure 5C:
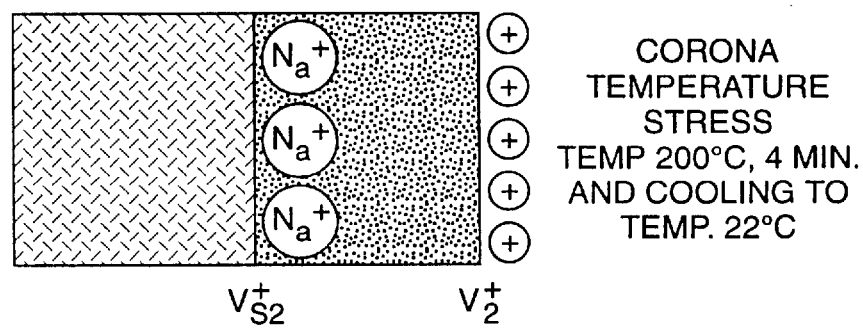
Figure 7:
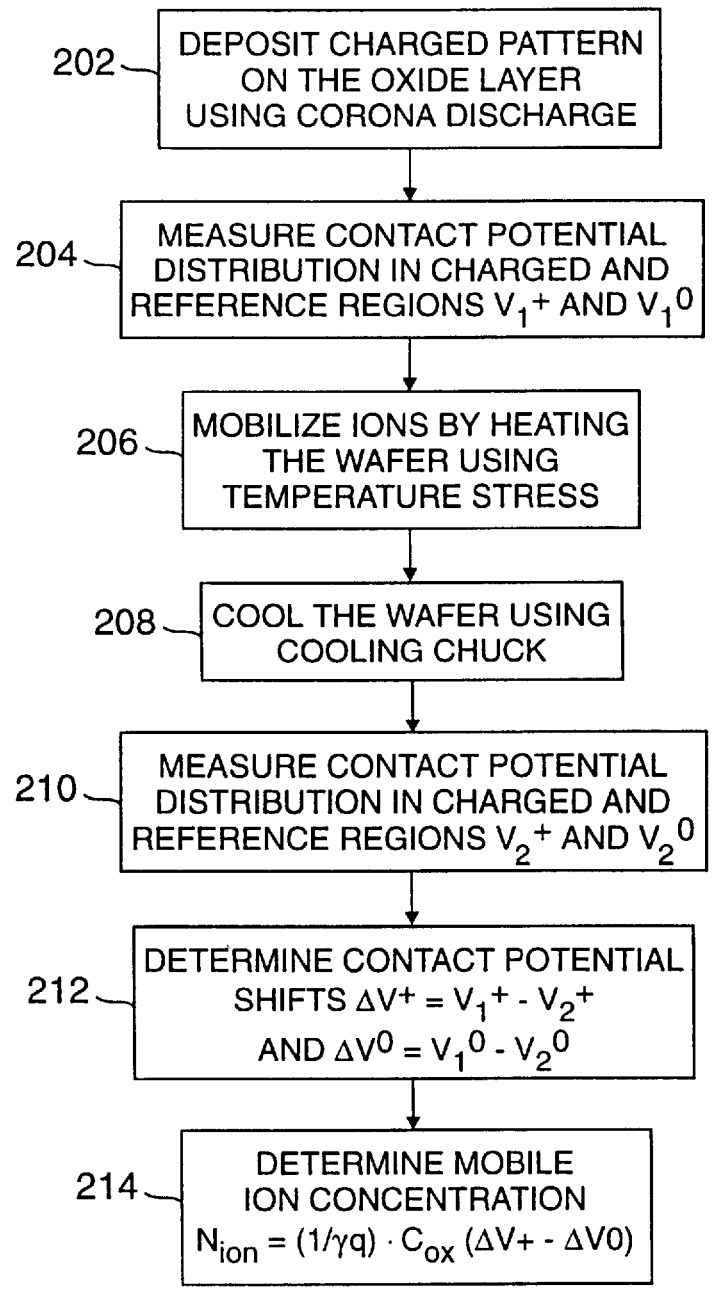
FIG. 7 is a flow diagram of a technique for measuring the mobile ion concentration in accordance with the invention.

Referring as well to FIG. 7, a flow chart illustrates the completely automated approach which has relatively few steps and, therefore, offers a relatively fast determination of mobile ion concentration with a measuring sequence corresponding to that of FIGS. 5A–5C. Silicon wafer 6 with an SiO$_2$ layer 4 is picked up from the cassette holder 14 by robotic handler 12. It is moved to a prealigner 16. After prealigning, wafer 6 is transported by robotic handler 12 to the wafer chuck 32 of the corona charging station 30. Rotation of wafer 6 is activated by motor 36 and a high DC positive voltage is applied to the corona discharge wire 42 for a predetermined period of time.

A predetermined corona charge is deposited on the top surface of the oxide in a pattern, shown in FIG. 9, containing charged regions 80, and reference region 82 (step 202). Wafer 6 is then transported by robot 12 to a measuring station 20 and the contact potential distribution is measured (with measuring device 22) in the form of a line scan across the wafer diameter giving the values of $V_1^+$ and $V_1^0$ in the charged and reference regions, respectively (step 204). Silicon wafer 6 is then moved by robotic handler 12 to temperature stress station 90. It is placed on the heated chuck and held at a temperature of e.g., 175° C. (to enhance the mobility of the ions) for a period e.g., approximately four minutes (step 206). The mobile, positive ions are repelled by the positive corona charge and drift toward the oxide/semiconductor interface (as shown in FIG. 5C). Wafer 6 is placed by robotic handler 12 on the cooling chuck and is cooled e.g., to room temperature (step 208). The wafer is then transported to measuring station 20 and contact potential distribution is measured with measuring device 22 (Step 210) along exactly the same lines as in step 204, giving the corresponding values $V_2^+$ and $V_2^0$ in the charged and reference regions, respectively. The difference between $V_1^+$ and $V_2^+$ provides the contact potential shift $\Delta V+$ and the difference between $V_2^0$ and $V_2^0$ provides the reference contact potential shift $\Delta V^0$ (step 212) which, as explained in detail below, are used in calculations to determine the mobile ion concentration (step 214). The calculation of the ion concentration (Step 214) involves the coefficient $\gamma$ which depends on the ion distribution. If during the $V_1^+$ measurement (Step 204, prior to temperature stress) the ions are located at the top of the oxide surface and after temperature stress they are at silicon/SiO$_2$ interface, then $\gamma=1$. If the ions were initially distributed in a uniform manner across the oxide thickness, $\gamma=0.5$. Discussion of $\gamma$ is given in D. K. Schroder "Semiconductor Material and Device Characterization", John Wiley & Sons, Inc., 1990, Ch. 6, p. 253, the entire contents of which is incorporated herein by reference.

Figure 8:
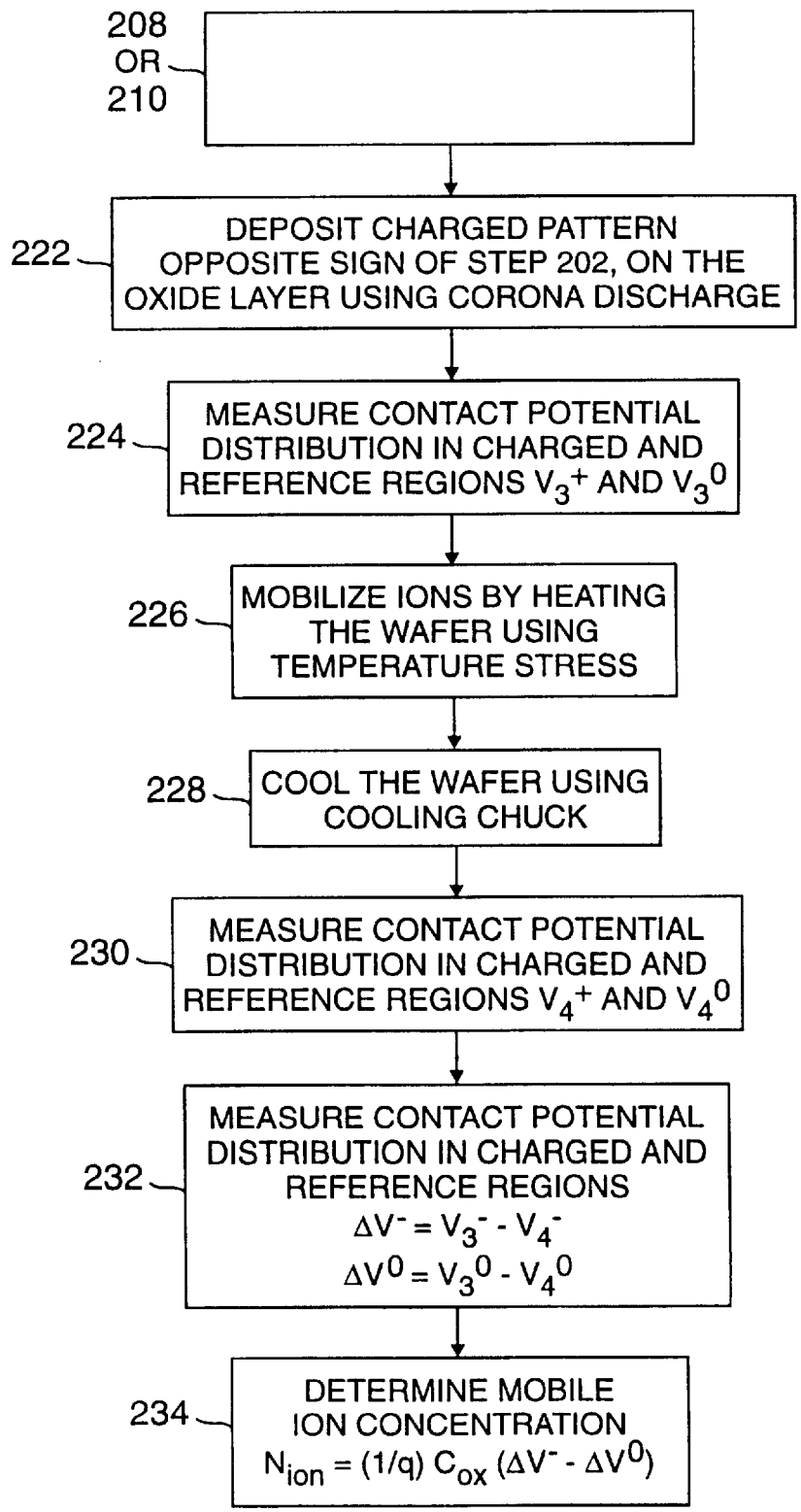
FIG. 8 is a flow diagram of another technique for measuring the mobile ion concentration in accordance with the invention.

Referring to FIG. 8, the uncertainty in y value and the accuracy of the method may be improved by adding second corona charging, moving the ions in a direction opposite of the first one. In the flow chart of FIG. 8, additional steps are added after Step 208 or after Step 210 in FIG. 7. If Step 202 involved positive corona charging then the new Step 222 in the sequence in FIG. 8 will involve negative corona charging of wafer 6. This negative corona must compensate for the previously deposited positive charge, therefore the negative charge should be approximately twice as large as that deposited in Step 202. Silicon wafer 6 is then moved to measuring station 20 and the contact potential distribution is measured with measuring device 22, giving the values of $V_3^-$ and $V_3^0$ in the charged and reference regions, respectively (Step 224) as also shown in FIG. 10. Wafer 6 is then moved by robotic handler 12 to the temperature stress station 90 where it is heated to e.g., 175° C. for four minutes to cause a motion of positive ions, attracted by the negative corona charge, toward the top of the oxide layer (step 226). Wafer 6 is then transported to measuring station 20 and the contact potential distribution is measured (Step 230) along exactly the same lines as in Step 224, giving the values $V_4^-$ and $V_4^0$ in the charged and reference regions, respectively, also shown in FIG. 9. The contact potential shift $\Delta V = V_3^- - V_4^-$ and the reference contact potential shift $\Delta V^0 = V_3^0 - V_4^0$ are calculated (Step 232) and the mobile ion concentration is determined (Step 234) from the contact potential shift $\Delta V - \Delta V^0$ as explained in detail below. The reference shift $\Delta V^0$ is taken as an average value for all points measured in the reference region. This shift represents a correction for the backside wafer charging as well as for water desorption (or adsorption). In an ideal case, $\Delta V^0 \approx$. The contact potential shift $\Delta V$ is position-dependent and changes corresponding to a distribution of the mobile ions. Note that in this sequence, step 204 and step 210 may be omitted and step 222 can follow step 208.

Figure 4A:
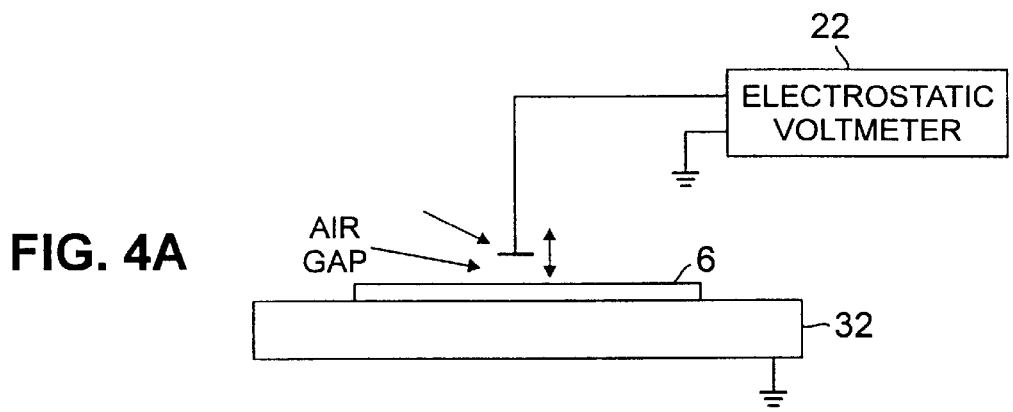
FIG. 4A is a side view schematic of a semiconductor wafer during contact potential measurement.
Figure 4B:
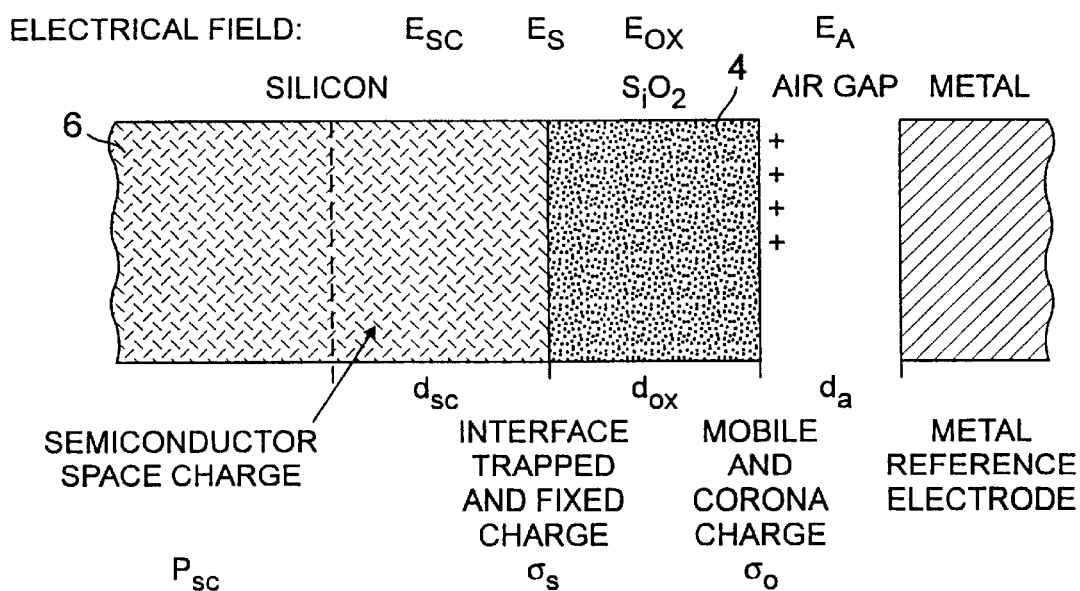
FIG. 4B is a cross sectional view of a semiconductor wafer having an oxide layer separated from a reference electrode by an air gap.
Figure 4C:
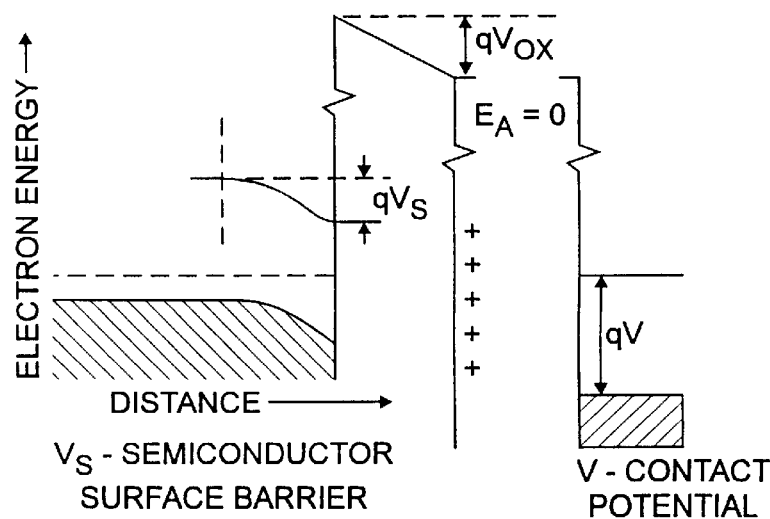
FIG. 4C is an energy band diagram corresponding to FIG. 4B.

The accuracy of the measurement can be further improved by complimenting all contact potential measurement steps (e.g., Steps 204, 210, 224, and 230) with corresponding SPV measurements of the surface potential barrier, $V_s$ (as shown in FIG. 4C and in FIG. 5). These measurements are done with measuring device 24 while wafer 6 is still on the measuring stage, immediately following contact potential measurement. For example, in the flow chart in FIG. 7, these additional steps would be giving the surface barrier value $V_{s1}^+$ in the charged region and $V_{s1}^0$ in the reference region, and Step 211, giving $V_{s2}^+$ and $V_{s2}^0$ for the charged and the reference regions, respectively. In the ideal case of no significant ion neutralization or charge injection into oxide during corona temperature stress, there is no significant surface barrier shift ($\leq 10$ mV for 100 Å oxide or $\leq 100$ mV for 1000 Å oxide). In this case, the surface barrier measurement confirms the validity of the approach and no corrections are needed in determining the mobile ion concentration. If surface barrier shifts are larger than 10 mV for thin oxides or 100 mV for thicker oxides, the corresponding corrections are introduced by subtracting surface barrier value shifts from the contact potential shifts.

Thus, the formula in Step 214 is replaced by:

$$N_{ion} = (1/\gamma q) \, C_{ox}(\Delta V^+ - \Delta V_s^+ - \Delta V^0 + \Delta V_s^0)$$

where:

$$\Delta V_s^+ = V_{s1}^+ - V_{s2}^+ \text{ and } \Delta V_s^0 = \Delta V_{s1}^0 - \Delta V_{s2}^0$$

Correspondingly, and referring to FIG. 8, Step 234 is replaced by:

$$N_{ion} = -(1/q) \, C_{ox}(\Delta V^- - \Delta V_s^- - \Delta V^0 + \Delta V_s^0)$$

where:

$$\Delta V_s^- = \Delta V_{s1}^- - V_{s2}^- \text{ and } \Delta V_s^0 = V_{s1}^0 - V_{s2}^0$$

The uncertainty of the approach increases when the surface barrier shifts are very large. This may be especially important for thin oxides and low mobile ion concentration when contact potential shifts associated with ion drifts are only a fraction of one volt. If the surface barrier shifts are comparable to or larger than contact potential shifts, the approach may be considered invalid due to a dominant role of interfering effects.

Theoretical Treatment and Calculations

The phenomena of mobile ion drift under corona temperature stress relates to measured quantities via the equations described in P. Edelman et al., "New Approach to Measuring Oxide Charge and Mobile Ion Concentration", SPIE-The International Society for Optical Engineering, Vol. 2337, pp. 154–164 (1994), incorporated herein as a reference.

The contact potential V in FIG. 5 is:

$$V = V_{ox} + V_s + \text{const.} \tag{1}$$

where:

$V_{ox}$ is the oxide potential barrier;

$V_s$ is the semiconductor surface potential barrier;

Const. is the constant depending on the work function of the metal used as a reference electrode in contact potential measurement.

$V_{ox}$ is the quantity which changes due to corona ion deposition and due to mobile ion drift across the oxide layer. $V_{ox}$ can be expressed as:

$$V_{ox} = \sigma_c/C_{ox} + \gamma \cdot \sigma_m/C_{ox} + \gamma_1 \cdot \sigma_1/C_{ox} \tag{2}$$

where:

$\sigma_c$ is the corona charge per unit surface area;

$\sigma_m = q$;

q is the elemental charge;

$\sigma_1$ is the surface density of other charges in oxide which are immobile;

$\gamma_1$ is the factor depending on the distribution of charges $\sigma_1$ throughout the oxide.

γ is the mobile charge distribution factor (the factor is discussed in D. K. Schroder, Semiconductor Material and Device Characterization; John Wiley & Sons, Inc., 1990; p. 254 the entire contents of which is incorporated by reference. γ=1 if all ions are near the top surface; γ=0 if all ions are near silicon/SiO$_2$ interface; and γ=½ when ions are distributed uniformly throughout the oxide thickness.)

$C_{ox}=K_{ox}\epsilon_0/d_{ox}$ is the oxide capacitance per unit surface area.

$K_{ox}$ is the dielectric constant of oxide ($K_{ox}$=3.9 for SiO$_2$);
$\epsilon_0$ is the permittivity of free space;
$d_{ox}$ is the oxide thickness.
$N_{ion}$ is the mobile ion surface charge density;
$N_{ion}$ is the mobile ion concentration per cm$^2$;

Mobile ion concentration is related to a change in $V_{ox}$ caused by ion drift by:

$$N_{ion}=(1/\gamma) \cdot C_{ox} \cdot (V_{ox}) \quad (3)$$

The corresponding numerical expression for SiO$_2$ is:

$$N_{ion[cm^{-2}]}=(2.15/\gamma) \cdot 10^{14} \cdot \Delta V_{ox}/d_{ox} \quad (4)$$

where $\Delta V_{ox}$ is in volts and $\Delta_{ox}$ is in [Å].

As pointed out above, $\Delta V_{ox}$ is determined as from the contact potential shift $\Delta V$ as:

$$\Delta V_{ox}=\Delta V-\Delta V_s$$

thus:

$$N_{ion}[cm^{-2}]=(2.15/\gamma)10^{14}(\Delta V-\Delta V_s)/d_{ox} \quad (5)$$

For the sequence in FIG. 8, $\Delta V=\Delta V^{--\Delta}V^0$ and γ=1; while for the sequence in FIG. 7, $\Delta V=\Delta V^{+-\Delta}V^0$ and γ=½.

Example:

Referring to FIG. 11b, the plots of the contact potential are provided for a 6-inch diameter silicon wafer with an SiO$_2$ layer approximately 4000Å thick on the wafer's top surface. Curve 102 represents initial contact potential distribution prior to any corona charging and temperature stress. After the sequence of Steps 202 through 208 in FIG. 7, a negative corona charging was done, as in Step 222, and curve 224 was measured, giving $V_3^-$ and $V_3^0$ in charged and reference regions. The temperature stress (Step 226) and cooling of the wafer (Step 228) was performed, after which curve 230 was measured, giving $V_4$ and $V_4^{-0}$, respectively. Pronounced contact potential shift is observed in the charged region and practically no change in the reference region (average $V_3^0$ and $V_4^0$ value was −0.2 volt). Complementary measurement of the surface barrier by surface photovoltage revealed $V_s$ shifts below 0.05 volts, insignificant in comparison to about 10 volt shifts in contact potential. The mobile $N_{ion}$ unit surface concentration was then calculated as $N_{ion} \approx -5.01 \times 10^{11} \times (V_3^- - V_4^- + 0.2)$; the resulting ion distribution is shown in FIG. 11a.

Other embodiments are within the appended claims.

What is claimed is:

1. A method for determining the mobile ion concentration within an oxide layer disposed on a surface of a semiconductor wafer, comprising:

a) depositing charge on at least a portion of the surface of the oxide layer at a low temperature at which said mobile ions do not substantially move, b) measuring the contact potential on the surface of the oxide layer at said low temperature, c) heating the semiconductor wafer and oxide layer to a temperature sufficient to activate the drift of said mobile ions, d) measuring the shift in contact potential after said heating, and e) determining the mobile ion concentration within the oxide layer on the basis of the shift.

2. The method of claim 1 further comprising:

measuring the contact potential on a portion of said wafer without deposited charge, and prior to said heating, measuring the contact potential barrier on said portion without deposited charge after said heating, and determining the mobile ion concentration on the basis of the contact potential difference in said portion of the surface of the oxide layer with said deposited charge on the basis of the shift in contact potential difference corrected on the basis of changing the contact potential difference in said portion without deposited charge.

3. The method of claim 1 comprising:

measuring the semiconductor surface potential barrier of said wafer before and after said heating, and determining the mobile ion concentration on the basis of said contact potential difference and the changes in said surface potential barrier before and after heating.

4. The method of claim 1 wherein the charge deposited on said portion of the surface of the oxide layer in step a) has a first polarity, the method further comprising:

depositing, charge of a second polarity, opposite of said first polarity, on said portion of the surface of the oxide layer to change the electric field in the oxide layer, and determining the mobile ion concentration on the basis of the contact potential differences determined with the charge of the first and second polarities.

5. The method of claim 4 comprising:

measuring the shift in contact potential after depositing the charge of said first polarity, measuring the shift in contact potential after depositing charge of said second polarity, and determining the mobile ion concentration on the basis of the difference in the shift in contact potential.

6. The method of claim 1 comprising measuring said contact potential prior to heating while the wafer is at room temperature.

7. The method of claim 1 comprising cooling the semiconductor wafer to a temperature at which said mobile ions do not substantially move after said heating and before said measuring.

8. The method of claim 1 comprising:

mapping the mobile ion concentration over a substantial area of said wafer.

9. The method of claim 1 comprising:

depositing charge over a substantial area of a wafer while leaving portions of said wafer without deposited charge.

10. The method of claim 1 comprising:

depositing said charge with a corona discharge.

11. The method of claim 1 comprising:

measuring said contact potential with a vibrating Kelvin probe voltmeter.

12. The method of claim 1 comprising:

measuring said contact potential with a Monroe-type sensor.

13. The method of claim 3 comprising:
the semiconductor surface potential barrier by SPV measurement.

14. The method of claim 3 comprising measuring the semiconductor surface potential barrier by non-contact SPV.

15. A system for the measurement of mobile contaminant ion concentration in an oxide layer of a semiconductor wafer, comprising:
- a charge deposition device configured to deposit charge on the oxide layer of the wafer;
- a temperature stress device including a element for heating the wafer to a temperature sufficient to allow mobile ions to drift; and
- a measurement device configured to measure the contact potential on the surface of the oxide layer prior to and after heating of the water by said element of said temperature stress device.

16. The system of claim 15 wherein said charge deposition device is a corona discharge apparatus constructed to deposit charge over a substantial area of said wafer while leaving portions without deposited charge.

17. The system of claim 16 wherein said corona discharge apparatus extends across the width of said wafer and includes shield regions to leave said portions without said charge.

18. The system of claim 15 wherein said measurement device is a Kelvin probe voltmeter.

19. The system of claim 15 wherein said measurement device is a Monroe-type sensor.

20. The system of claim 15 wherein said temperature stress device includes a cooling element for cooling the wafer to a temperature at which said mobile ions do not substantially move.

21. The system of claim 15 further comprising a robotic handler configured to move the semiconductor wafer between the charge deposition device, temperature stress device, and measurement device.

22. The system of claim 21 further comprising a computer adapted to control the robotic handler and to transmit control signals to and receive data signals from the charge deposition device, temperature stress device, and measurement device.

23. The system of claim 15 further comprising a device for measuring the surface potential barrier.

24. The method of claim 1 wherein the depositing step includes depositing charge on only a portion of a free surface of the oxide layer.

* * * * *